United States Patent [19]

Shealy et al.

[11] Patent Number: 4,611,074

[45] Date of Patent: Sep. 9, 1986

[54] (ALKYLSULFONYL)METHANESULFONATES AS ANTICANCER AGENTS

[75] Inventors: Y. Fulmer Shealy; Charles A. Krauth, both of Birmingham, Ala.

[73] Assignee: Southern Research Institute, Birmingham, Ala.

[21] Appl. No.: 672,831

[22] Filed: Nov. 19, 1984

Related U.S. Application Data

[63] Continuation-in-part of Ser. No. 558,435, Dec. 6, 1983, abandoned.

[51] Int. Cl.$^4$ .......................................... C07C 143/68
[52] U.S. Cl. ..................................................... 558/51
[58] Field of Search .................................... 260/456 R

[56] References Cited

PUBLICATIONS

Shealy et al., J. Med. Chem., 26, 1168 (1983).

Senning et al., Arznei.-Forsch., 26, 1800 (1976).
Shealy et al., Chem. Abstr., 100, 150700a (1984).

*Primary Examiner*—Nicky Chan
*Attorney, Agent, or Firm*—Roylance, Abrams, Berdo & Goodman

[57] ABSTRACT

Compounds of the formula:

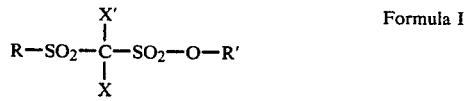

Formula I wherein R is methyl or other lower alkyl group; X and X' individually are hydrogen or lower alkyl; and R' is a 2-haloethyl group or other halogenated lower alkyl group are useful in the treatment of neoplastic diseases.

11 Claims, No Drawings

(ALKYLSULFONYL)METHANESULFONATES AS ANTICANCER AGENTS

CROSS-REFERENCE TO RELATED APPLICATION

This application is a continuation-in-part of application Ser. No. 558,435, filed Dec. 6, 1983, now abandoned.

BACKGROUND OF THE INVENTION

This invention relates to compounds that are esters of (alkylsulfonyl)methanesulfonic acids which are useful in the treatment of neoplastic diseases.

A recent article entitled "2-Haloethylating Agents for Cancer Chemotherapy. 2-Haloethyl Sulfonates" by Y. F. Shealy et al. in *Journal of Medicinal Chemistry* (1983), Vol. 26, pages 1168–1173, reports investigations of various 2-haloethyl sulfonates as potential anticancer agents. Included among these various 2-haloethyl sulfonates were 2-chloroethyl methanesulfonate which is the prototype 2-haloethyl sulfonate in the area of experimental cancer chemotherapy. This compound has the formula $CH_3$—$SO_2$—O—$CH_2CH_2$—Cl. In the studies described in this article, the most active compound in tests against P388 leukemia in mice, the primary screening test of the National Cancer Institute, was 2-chloroethyl chloromethanesulfonate, i.e., $ClCH_2$—$SO_2$—O—$CH_2CH_2$—Cl.

Senning et al. in *Arznei.-Forsch.*, Vol. 26, pages 1800–1809 (1976) report the preparation and testing for antileukemic activity in animals of methyl (methylsulfonyl)methanesulfonate, i.e., the compound $CH_3SO_2CH_2SO_2OCH_3$.

SUMMARY OF THE INVENTION

It has now been found that certain halogenated esters of (alkylsulfonyl)methanesulfonic acids are particularly effective in the treatment of neoplastic diseases. The compounds of this invention are represented by the formula:

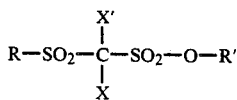

Formula I wherein R is methyl or other lower alkyl group; X and X' individually are hydrogen or lower alkyl; and R' is a 2-haloethyl group or other halogenated lower alkyl group. As used herein, the term "lower alkyl" refers to alkyl groups containing six or less carbon atoms.

Especially preferred compounds are 2-chloroethyl (methylsulfonyl)methanesulfonate, i.e., $CH_3SO_2CH_2SO_2OCH_2CH_2Cl$; 2-fluoroethyl (methylsulfonyl)methanesulfonate, i.e., $CH_3SO_2CH_2SO_2OCH_2CH_2F$; and 2-bromoethyl (methylsulfonyl)methanesulfonate, i.e., $CH_3SO_2CH_2SO_2OCH_2CH_2Br$.

DETAILED DESCRIPTION OF THE INVENTION

In the following discussion, Formulas II to V are referred to. These formulas are as follows:

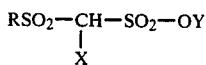

Formula II

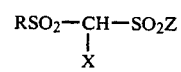

Formula III

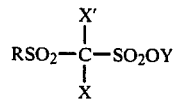

Formula IV

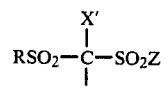

Formula V

The compounds of this invention in which R is a methyl group and X and X' are hydrogen are prepared by treating (methylsulfonyl)methanesulfonyl chloride (Formula III with R=methyl, X=hydrogen, and Z=Cl) with the appropriate alcohol in the presence of a tertiary amine in an appropriate solvent. (Methylsulfonyl)methanesulfonyl chloride may be prepared by treating sodium (methylsulfonyl)methanesulfonate (Formula II with R=methyl, X=hydrogen, and Y=Na) with phosphorus pentachloride and phosphorus oxychloride. The preparation of sodium (methylsulfonyl)methanesulfonate from methanesulfonyl chloride has been described by Senning, *Synthesis*, pages 211–212 (1973).

Other compounds of this invention are prepared similarly from an appropriately substituted sulfonic acid (Formula II with Y=H) or sulfonic acid salt (Formula II with Y=a metal ion). Such precursors may be prepared by various methods. For example, alkylation of a sulfonyl-sulfonic acid derivative (Formula II with X=H and Y=a metal ion or an aryl group) will provide an alkyl derivative (Formula II with X=alkyl). Also, dialkylation of such a compound of Formula II with X=H or monoalkylation of such a compound of Formula II with X=an alkyl group or an aryl group will provide a dialkyl or an alkyl aryl sulfonyl-sulfonic acid derivative represented by Formula IV in which X is a lower alkyl group and X' is an alkyl or an aryl group. The following examples are illustrative. Sodium 1-(methylsulfonyl)ethanesulfonate (Formula II with X=R=methyl and Y=Na) is prepared by base-catalyzed methylation of sodium (methylsulfonyl)methanesulfonate (Formula II; R=$CH_3$, X=H, Y=Na) with methyl iodide. The dialkylation product (e.g., Formula IV with X=X'=$CH_3$) may also be obtained from such an alkylation. Sodium 1-methyl-1-(methylsulfonyl)ethanesulfonate (Formula IV with X=X'=R=$CH_3$ and Y=Na), a dialkylation product, is prepared by base-catalyzed methylation of the monomethyl derivative (Formula II with X=R=$CH_3$ and Y=Na).

The alkyl, dialkyl, or alkyl aryl substituted sulfonyl-sulfonic acids or their salts represented by Formulas II and IV may be converted to sulfonyl halides represented by Formula III with X=alkyl, R=methyl, and Z=a halogen or Formula V with X=alkyl, X'=alkyl or aryl, R=methyl, and Z=a halogen. These sulfonyl halides are then treated with the appropriate 2-haloethanol and a tertiary amine in order to obtain the desired 2-haloethyl sulfonates of Formula I wherein X=an alkyl group, X'=hydrogen, and R=methyl or Formula I wherein X=an alkyl group, X'=alkyl or aryl group, and R=methyl. Thus, 2-chloroethyl 1-(methylsulfonyl)ethanesulfonate (Formula I with X=R=methyl, X'=hydrogen and R'2-chloroethyl) and 2-chloroethyl 1-methyl-1-(methylsulfonyl)ethanesulfonate (Formula I with $X=X'=R=$methyl and $R'=$2-chloroethyl) are prepared as outlined and illustrate the 2-haloethyl 1-substituted (methylsulfonyl)methanesulfonates.

The foregoing examples demonstrate that (methylsulfonyl)methanesulfonate salts (Formula II with $Y =$ a metal ion) and (methylsulfonyl)methanesulfonyl halides (e.g., Formula III with $Z=Cl$) may be employed as isolated compounds and as common precursors in syntheses of *various* (methylsulfonyl)methanesulfonate esters, such as the 2-haloethyl esters of Formula I. Alternatively, the aforementioned 2-haloethyl (methylsulfonyl)methanesulfonates of Formula I with $R=$methyl and $X=X'=$hydrogen may be prepared by a one-step operation. This simpler and improved one-step synthesis consists of the treatment of methanesulfonyl chloride in an anhydrous, inert solvent and at low temperatures with a tertiary amine followed by the addition to this reaction mixture of the appropriate 2-haloethanol. This method is illustrated (Example 10) by the synthesis of 2-chloroethyl (methylsulfonyl)methanesulfonate (Formula I with $R=$methyl, $X=X'=$hydrogen, and $R'=$2-chloroethyl) by the treatment of methanesulfonyl chloride in anhydrous acetonitrile at $-30°$ to $-40°$ C. with triethylamine and the addition to the resulting reaction mixture of 2-chloroethanol. This one-step synthesis can replace the three-step synthesis described above. The three steps that are replaced are the following: (1) the preparation and isolation of sodium (methylsulfonyl)methanesulfonate; (2) the preparation and isolation of (methylsulfonyl)methanesulfonyl chloride; (3) the preparation of the 2-haloethyl esters from the sulfonyl chloride. The yield of 2-chloroethyl(methylsulfonyl)methanesulfonate obtained by the one-step synthesis from methanesulfonyl chloride is higher than the yield of the same 2-chloroethyl ester obtained by the three-step synthesis from the same starting material. The one-step synthesis may be employed for the synthesis of a variety of esters (Formula I with $R=$methyl, $X=X'=$hydrogen, and $R'$ various alkyl, substituted-alkyl, aryl, or aralkyl groups), in addition to 2-haloethyl esters, of (methylsulfonyl)methanesulfonic acid.

The compounds of this invention are potential 2-haloethylating agents. 2-Haloethylating agents act by attaching a 2-haloethyl group to a nucleophilic center of a substrate; i.e., they react at the carbon atom of the 2-haloethyl group that is remote from the halogen group. This type of agent differs, therefore, from nitrogen mustards, which also contain 2-haloethyl groups. Nitrogen mustards, in contrast to 2-haloethylating agents, react at the carbon atom bearing the halogen, and this alkylation reaction results in displacement of the halogen.

Tests of certain (methylsulfonyl)methanesulfonates against certain malignancies in mice revealed that they are active in inhibiting these diseases and may markedly increase the life span of treated animals. Thus, treatment of mice bearing P388 leukemia, L1210 leukemia, B16 melanoma, or Lewis lung carcinoma with 2-chloroethyl (methylsulfonyl)methanesulfonate (Example 2; Formula I with $R=CH_3$, $X=X'=H$, and $R'=CH_2CH_2Cl$) resulted in the survival of some of the treated mice until the tests were terminated after 60 days. In contrast, the median survival times of groups of untreated control mice bearing P388 leukemia, L1210 leukemia, B16 melanoma, or Lewis lung carcinoma were 10.5–13 days, 8.3–8.5 days, 17.4–18.1 days, and 16.3–21.1 days, respectively. The treated animals that survived until the tests were terminated after 60 days, may be regarded as free, or cured, of the malignancy.

Therapeutic compositions containing compounds of Formula I are useful for ameliorating cancer diseases in mammals. The active ingredients of the therapeutic compositions inhibit transplanted mouse tumor growth when administered in amounts ranging from about 5 mg to about 200 mg per kilogram of body weight per day. A preferred dosage regimen for optimum results would be from about 5 mg to about 50 mg per kilogram of body weight per day, and such dosage units are employed that a total of from about 350 mg to about 3.5 grams of the active compound for a subject of about 70 kg of body weight are administered in a 24-hour period. This dosage regimen may be adjusted to provide the optimum therapeutic response. For example, several divided doses may be administered daily or the dose may be proportionally reduced as indicated by the exigencies of the therapeutic situation. A decided practical advantage is that the active compound may be administered in any convenient manner such as by the oral, intravenous, intramuscular, intraperitoneal or subcutaneous routes.

The following examples illustrate modes contemplated for carrying out this invention. In the examples illustrating syntheses of the compounds of this invention, data were acquired and are reported as follows. Decomposition and melting temperatures (mp) were determined in capillary tubes. Infrared spectra (IR) were recorded from samples in pressed potassium bromide discs; s=strong, sh=shoulder, w=weak. Mass spectral data (MS) were taken from low-resolution, electron-impact spectra determined at 70 eV unless indicated otherwise. The peaks listed are those arising from the molecular ion (M), those attributable to the loss of certain fragments (M minus a fragment), and certain other prominent peaks. Nuclear magnetic resonance spectra were determined at 100 MHz for proton ($^1$H NMR) spectra unless indicated otherwise. The internal reference was tetramethylsilane; s=singlet, t=triplet, m=multiplet, q=quartet.

EXAMPLE 1

(Methylsulfonyl)methanesulfonyl Chloride (Formula III with $Z=Cl$, $X=H$ and $R=CH_3$)

Phosphorus pentachloride (79.3 g, 0.381 mole) and sodium (methylsulfonyl)methanesulfonate (Formula II with $Y=Na$, $X=H$ and $R=CH_3$; 70 g, 0.359 mole) were stirred with 150 ml of phosphorus oxychloride. As the mixture was warmed to 70° C. in an oil bath, hydrogen chloride was slowly evolved, and the slurry thinned enough to be stirred with a magnetic stirrer. The mixture was heated for 18 hours in an oil bath at 80°–90° C., cooled, and filtered, and the residue was washed with dry chloroform. The chloroform caused the product to precipitate in the filtrate. The precipitate was collected, washed with a small amount of chloroform, and dried over sodium hydroxide pellets: yield, 28.5 g (41%); mp 109°–111° C.; MS (direct-probe temperature, 20° C.) m/e 193 (M+H), 192 (M), 177 (M-CH$_3$), 157 (CH$_3$SO$_2$CH$_2$SO$_2$), 143, 141, 113 (CH$_2$SO$_2$Cl), 98 (CH$_3$SOCl), 94, 93 (CH$_3$SO$_2$CH$_2$), 79 (CH$_3$SO$_2$), 78, 64, 63 (CH$_3$SO); IR (cm$^{-1}$, strong and medium bands) 3045, 3025, 2995 s, 2930 s, 1405, 1390 s, 1380 s, 1360, 1335 s, 1325 sh, 1315 s, 1225, 1175 s, 1160 s, 1110 s, 980 s, 965, 860 s, 760 s, 695, 595 s, 515 s, 495 s, 460 s.

Two additional crops were obtained. One was obtained by washing the chloroform-washed residue with ethyl acetate, evaporating the solvent, and crystallizing the residue from ethyl acetate and hexane: weight 3.9 g (6%); mp 108°–110° C. Another crop was obtained from the original filtrate after it had been chilled in a refrigerator overnight: yield, 9.0 g (13%); mp 107°–110° C. The total amount of product that was suitable for conversion to esters was 41 g (60%).

EXAMPLE 2

2-Chloroethyl (Methylsulfonyl)methanesulfonate
(Formula I with R=CH$_3$, X=X'=H and
R'=2-chloroethyl)

A solution, protected from atmospheric moisture, of 21 g (109 mmoles) of (methylsulfonyl)methanesulfonyl chloride in 130 ml of dry ethyl acetate was chilled in an ice bath. A mixture of 9.7 g (120 mmoles) of 2-chloroethanol and 14.0 g (138 mmoles) of triethylamine was added dropwise (during 0.5 hour) to the well-stirred methanesulfonyl chloride solution. The reaction mixture was stirred for 3 hours in an ice bath and then stored in a refrigerator overnight. The triethylamine hydrochloride was separated by filtration and washed with ethyl acetate. The filtrate (plus washings) was washed three times with saturated NaCl solution, dried (MgSO$_4$), and concentrated to a waxy solid: weight, 22.5 g. The crude product was mixed well with hot benzene (300 ml), the hot mixture was filtered, and the residue was extracted with a second portion (100 ml) of hot benzene. The two filtrates were combined, and the benzene solution was diluted with hexane. The resulting precipitate was collected by filtration, washed with hexane, and dried in vacuo: weight, 19.5 g; mp 56°–58° C. The crude product was dissolved in hot benzene (22 ml/g), and the warm (50° C.) solution was diluted with an equal volume of hexane. After considerable crystallization had occurred, warm hexane (2 additional volumes/volume of benzene) was added with stirring. The mixture was allowed to cool, chilled at −20° C. (2 hours), and filtered. The crystalline material was separated by filtration, washed with hexane, and dried in vacuo: yield, 66%; mp 58°–60° C. This product contained a small amount of a nitrogen-containing, chloroform-soluble impurity. A mixture of this material and chloroform (3.75 ml/g) was stirred under a nitrogen atmosphere for 40 minutes and then filtered. The undissolved material was washed with chloroform and dried; mp 59.5°–62° C. This material was treated in the same way with chloroform (2.4 ml/g) for 50 minutes: yield, 45%; mp 60.5°–62° C.; TLC, 1 spot (developed with 1:1 hexane-ethyl acetate, detection with iodine vapor); MS (direct-probe temperature, 20° C.) m/e 237 (M+H), 201 (M-Cl), 200 (M-HCl), 187 (M-CH$_2$Cl), 175 (CH$_3$SO$_2$CH$_2$SO$_3$+2H), 157 (CH$_3$SO$_2$CH$_2$SO$_2$), 142 (ClCH$_2$CH$_2$OSO$_2$—H), 127 (ClCH$_2$CH$_2$OSO), 109, 96, 94, 93 (CH$_3$SO$_2$CH$_2$), 80, 79 (CH$_3$SO$_2$) 65, 63 (CH$_3$SO and ClCH$_2$CH$_2$), 62 (CH$_2$=CHCl); IR (cm$^{-1}$, medium and strong bands) 3040, 3025, 2990 s, 2930, 2935 sh, 1465, 1430, 1415, 1390, 1370 s, 1320 s, 1240, 1200, 1185 s, 1175 s, 1165 s, 1160 sh, 1125, 1070, 990 s, 955 s, 920 s, 870 s, 790 s, 765, 755, 665, 600, 530 s, 505, 465 s, 420; $^1$H NMR (CDCl$_3$) $\delta$3.25 (s, CH$_3$), 3.79 (t, O CH$_2$Cl), 4.65 (t, OCH$_2$), 4.68 (s, SCH$_2$S); $^{13}$C NMR (CDCl$_3$)$\delta$40.95, 42.30, 68.78, 72.34. Anal. Calcd. for C$_4$H$_9$ClO$_5$S$_2$: C, 20.30; H, 3.83. Found: C, 20.37; H, 3.95

EXAMPLE 3

2-Fluoroethyl (Methylsulfonyl)methanesulfonate
(Formula I with R=CH$_3$, X=X'=H and
R'=2-fluoroethyl)

The process of Example 2 was repeated using 5 g (26 mmoles) of (methylsulfonyl)methanesulfonyl chloride and 1.8 g (28.6 mmoles) of 2-fluoroethanol, 3.3 g (33 mmoles) of triethylamine and 30 ml of ethyl acetate. There was thus obtained the desired product as a viscous oil. A solution of the crude product (4.9 g) in ethyl acetate was filtered and diluted slowly with hexane. The oil that separated initially was induced to crystallize, and the mixture was chilled in an ice bath. The precipitate was collected by filtration, washed with hexane, and dried in vacuo over P$_2$O$_5$: yield, 3.79 g (65%); mp 50°–52° C. dec; TLC, 1 spot (developed with 1:1 hexane-ethyl acetate, detection with iodine vapor); MS (direct-probe temperature, 20° C.) m/e 221 (M+H), 201 (M-F), 200 (M-HF), 187 (M-CH$_2$F), 175 (CH$_3$SO$_2$CH$_2$SO$_3$+2H), 157 (CH$_3$SO$_2$CH$_2$SO$_2$), 142, 126, 122, 111, 109, 96, 95, 94, 93 (CH$_3$SO$_2$CH$_2$), 80, 79 (CH$_3$SO$_2$), 65, 63 (CH$_3$SO), 46 (CH$_2$=CHF); IR (cm$^{-1}$, medium and strong bands) 3030, 3020, 3000 s, 2975, 2935 s, 1450, 1420, 1385 s, 1365 s, 1330 s, 1300 s, 1265, 1245, 1190 s, 1150, 1140 s, 1060 s, 1015 s, 980, 930 s, 875 s, 810 s, 785, 715, 595, 535, 505 s, 470 s, 445 s; $^1$H NMR (CDCl$_3$)$\delta$3.25 (s, CH$_3$), 4.69 (s, SCH$_2$S), 4.40–5.05 (m, CH$_2$CH$_2$F, AA'BB'X system). Anal. Calcd. for C$_4$H$_9$FO$_5$S$_2$: C, 21.81; H, 4.12. Found: C, 21.69; H, 4.27

EXAMPLE 4

2-Bromoethyl (Methylsulfonyl)methanesulfonate
(Formula I with R=CH$_3$, X=X'=H and
R'=2-bromoethyl)

The title compound was obtained by the process of Example 2 from (methylsulfonyl)methanesulfonyl chloride and 2-bromoethanol. The crude yellow solid was triturated with chloroform, and the resulting white solid was dried in vacuo: yield, 50%; mp 63°–65° C.; TLC, 1 spot (developed with 2:1 hexane-ethyl acetate, detection with iodine vapor or 4-nitrobenzylpyridine spray); MS (direct-probe temperature, 20° C.) m/e 281 (M+H), 201 (M-Br), 187 (M-CH$_2$Br), 175 (CH$_3$SO$_2$CH$_2$SO$_3$+2H), 157 (CH$_3$SO$_2$CH$_2$SO$_2$), 123, 121, 106 (CH$_2$=CHBr), 94, 93 (CH$_3$SO$_2$CH$_2$), 80, 79 (CH$_3$SO$_2$), 63 (CH$_3$SO); IR (cm$^{-1}$, medium and strong bands) 3040, 3025, 2990 s, 2930, 2935 sh, 1460, 1425, 1415, 1390, 1370 s, 1320 s, 1280, 1240, 1190 s, 1170 sh, 1165 s, 1125 s, 1060, 970 s, 945 s, 900 s, 870 s, 785 s, 765, 755, 700, 600, 570, 525 s, 505, 465 s, 400; $^1$H NMR (CDCl$_3$)$\delta$3.25 (s, CH$_3$), 3.61 (t, CH$_2$Br), 4.69 (s, SCH$_2$S), 4.70 (t, OCH$_2$) Anal. Calcd. for C$_4$H$_9$BrO$_5$S$_2$: C, 17.09; H, 3.23. Found: C, 17.14; H, 3.34.

EXAMPLE 5

Methyl (Methylsulfonyl)methanesulfonate (Formula I
with R=R'=CH$_3$ and X=X'=H)

The title compound was obtained by reacting (methylsulfonyl)methanesulfonyl chloride with methanol according to the procedure of Example 2. The reaction mixture was stored in a refrigerator overnight. The supernatant solution was decanted from an amorphous precipitate, and the residue was triturated with three portions of ethyl acetate. The four ethyl acetate solutions were combined, and the resulting solution was washed with NaCl solution, dried (MgSO$_4$), and concentrated to dryness in vacuo: yield, 37%; mp 101°–104° C. (lit. Senning et al., supra, 94°–98° C.); MS (direct-probe temperature, 180° C.) m/e 189 (M+H), 175 (CH$_3$SO$_2$CH$_2$SO$_3$+2H), 173 (M-CH$_3$), 157 (CH$_3$SO$_2$CH$_2$SO$_2$), 143, 124, 110, 109, 94, 93 (CH$_3$SO$_2$CH$_2$), 80, 79 (CH$_3$SO$_2$), 65, 63 (CH$_3$SO); IR (cm$^{-1}$, medium and strong bands) 3040, 3015, 2995 s, 2935, 1450, 1415, 1385 sh, 1380 s, 1365, 1310 s, 1307 s, 1240 s, 1190 s, 1160 s, 1125, 1120, 1045, 980 s, 820, 800 s, 760, 695, 610, 580, 520, 505, 475, 450; $^1$H NMR (CDCl$_3$)δ3.25 (s, CH$_3$SO$_2$), 4.10 (s, OCH$_3$), 4.59 (s, SCH$_2$S). Anal. Calcd. for C$_3$H$_8$O$_5$S$_2$: C, 19.14; H 4.28. Found: C, 19.05; H, 4.42.

EXAMPLE 6

Sodium 1-(Methylsulfonyl)ethanesulfonate (Formula II, X=R=CH$_3$, Y=Na) and Sodium 1-Methyl-1-(methylsulfonyl)ethanesulfonate (Formula IV with R=X=X'=CH$_3$ and Y=Na)

A mixture of sodium (methylsulfonyl)methanesulfonate (Formula II with R=CH$_3$, X=H and Y=Na; 60 g) and dry dimethylformamide (1500 ml) was heated to 40° C. to effect dissolution of most of the sodium salt. The mixture was cooled to room temperature, and sodium hydride (15 g) dispersed in mineral oil (50% NaH) was added. The resulting mixture was stirred at room temperature for 0.5 hour, heated at 40°–50° C. for 2 hours, and cooled to room temperature. Methyl iodide (19.7 ml) was added in three portions, and the resulting mixture was stirred for 1 hour after each addition, the temperature being at 40°–50° C. during the last two additions. The mixture was then stirred at room temperature overnight, filtered, and concentrated in vacuo to a solid residue. The residue was mixed with acetone (1.5 l) containing a small amount (ca. 150 ml) of ethyl acetate. The mixture was stirred for 1.5 hr., and the suspended solid was collected by filtration, washed with acetone, and dried; weight, 39 g. The filtrate was concentrated in vacuo to dryness, the residue was dissolved in water (300 ml), the water solution was filtered and diluted with ethanol (1200 ml), and this solution was stored overnight in a refrigerator. A precipitate was collected by filtration, washed with ethanol, and dried in vacuo; weight, 17.5 g. The mass spectrum by the fast-atom-bombardment method (FAB) and the proton NMR spectrum showed that this material was sodium 1-(methylsulfonyl)ethanesulfonate (Formula II, X=R=CH$_3$, Y=Na) containing a small amount of sodium 1-methyl-1-(methylsulfonyl)ethanesulfonate (Formula IV, X=X'=R=CH$_3$, Y=Na): positive FAB MS, m/e 443 (2M+Na), 233 (M+Na), 325 (233+glycerol), 417 (325+glycerol); negative FAB MS m/e 397 (2M - Na), 187 (M - Na); $^1$H NMR (300.6 MHz, Me$_2$SO-D$_6$, Me$_4$Si as internal reference) δ1.48 (d, CH$_3$CH, 3.11 (s, CH$_3$SO$_2$), 4.06 (q, CHCH$_3$). The infrared spectrum (KBr) included strong bands at 1305, 1265, 1240, 1200, 1140, 1045, 750 and 530 cm$^{-1}$. A portion (7.0 g) of this material was recrystallized from ethanol: recovery of white crystals, 78.6% (5.5 g); mp 197°–203° C. dec. Anal. Calcd. for C$_3$H$_7$O$_5$S$_2$Na: C, 17.14; H, 3.36. Found: C, 17.10; H, 3.77.

The portion of the solid (39 g) filtered from the acetone-ethyl acetate slurry (described above) was triturated with ethanol, and the solid phase was collected by filtration and dried in vacuo; weight, 31 g. The mass spectrum by the fast-atom-bombardment method (FAB) and the proton NMR spectrum showed that this material was sodium 1-methyl-1(methylsulfonyl)ethanesulfonate (Formula IV with X=X'=R=CH$_3$ and Y=Na) containing a small amount of sodium 1-(methylsulfonyl)ethanesulfonate: positive FAB MS, m/e 247 (Na+M of IV with X=X'=R=CH$_3$ and Y=Na), 339 (247+glycerol), 233 (M of sodium 1-(methylsulfonyl)ethanesulfonate+Na); negative FAB MS, m/e 425 (2M - Na), 201 (M - Na), 187 (M of 1-(methylsulfonyl)ethanesulfonate - Na); $^1$H NMR (Me$_2$SO-D$_6$), Me$_4$Si as internal reference; major peaks), δ1.50 ((CH$_3$)$_2$C), 3.09 (CH$_3$SO$_2$). The infrared spectrum (KBr) included strong bands at 1310, 1295 sh, 1220, 1120, 1045, 730 and 545 cm and also included weak bands indicative of the presence of sodium 1-(methylsulfonyl)ethanesulfonate.

EXAMPLE 7

1-(Methylsulfonyl)ethanesulfonyl Chloride (Formula III with X=R=CH$_3$ and Z=Cl)

A mixture of 5 g of sodium 1-(methylsulfonyl)ethanesulfonate (Formula II, X=R=CH$_3$, Y=Na) and 5.34 g of phosphorus pentachloride was stirred under an inert atmosphere at room temperature. After about 20 minutes, the evolution of hydrogen chloride and the generation of heat were observed, and shortly thereafter the mixture became liquid. The mixture was maintained at 80°–100° C. overnight, cooled, and diluted with dichloromethane. The mixture was filtered, the residue was washed with dichloromethane, and the solvent was evaporated from the dichloromethane solution (combined portions) with a stream of nitrogen. The residual oil was concentrated further with a vacuum pump: weight of oil, 3.8 g. The mass spectrum and the proton NMR showed that this material was principally 1-(methylsulfonyl)ethanesulfonyl chloride (Formula III, R=X=CH$_3$ and Z=Cl): MS (electron-impact, direct-probe temperature 20° C.), m/e 207 (M+1), 171 (M - Cl); $^1$H NMR (300.6 MHz, CDCl$_3$), δ2.07 (d, CH$_3$CH), 3.32 (s, CH$_3$SO$_2$), 4.84 (q, CHCH$_3$). The infrared spectrum (KBr) included strong bands at 1375, 1325, 1170, 1150, 960, 760, 715, 595, 535, 505, 490 cm$^{-1}$.

EXAMPLE 8

2-Choroethyl 1-(Methylsulfonyl)ethanesulfonate (Formula I with R=X=CH$_3$, X'=hydrogen and R'=2-Chloroethyl)

A solution of triethylamine (1.6 ml), 2-chloroethanol (0.86 ml), and ethyl acetate (2 ml) was added dropwise during 10 minutes to a solution of 1-(methylsulfonyl)ethanesulfonyl chloride (2.0 g) in ethyl acetate (10 ml). The latter solution was kept in an ice bath during the addition, and the reaction mixture was stirred at ice-bath temperatures for 2 hours. Triethylamine hydrochloride was separated by filtration and washed with ethyl acetate (2×30 ml). The filtrate (including washings) was washed with sodium chloride solution, dried, filtered, and concentrated in vacuo to an oil (2.2 g). The crude product was purified by flash chromatography on a column of silica gel with 2:1 hexane-ethyl acetate as the eluting and developing solvent. Product-containing fractions (determined by TLC) were combined, the solvents were evaporated under reduced pressure, and the residue was kept under greatly reduced pressure (vacuum pump) overnight. The residual oil (1.68 g, 69% yield) solidified while it was kept for 48 hr. in a vacuum (vacuum pump). This material was recrystallized from ethyl acetate-cyclohexane: yield, 46% (1.12 g); mp 67-°69° C.; MS (electron-impact, direct-probe temperature 20° C.), m/e 251 (M+1), 215 (M - Cl), 214 (M - HCl), 201 (M - CH$_2$Cl), 171, 159, 142; $^1$H NMR (300.6 MHz, CDCl$_3$, Me$_4$Si as internal reference), δ1.92 (d, CH$_3$CH), 3.33 (s, CH$_3$SO$_2$), 3.80 (t, CH$_2$Cl), 4.51 (q, C$\underline{H}$CH$_3$), 4.64 (t, OCH$_2$); IR (strong bands) 2935, 1365, 1330, 1310, 1300, 1180, 1140, 995, 945, 900, 780, 775, 520, 470. Anal. Calcd. for C$_5$H$_{11}$ClO$_5$S$_2$: z C, 23.95; H, 4.42. Found: C, 23.94; H, 4.56.

EXAMPLE 9

Sodium 1-Methyl-1-(methylsulfonyl)ethanesulfonate (Formula IV, R=X=X'=CH$_3$, Y=Na).

Sodium 1-(methylsulfonyl)ethanesulfonate (Formula II with X=R=CH$_3$ and Y=Na; 5.0 g) was dissolved in dry dimethylformamide (125 ml); sodium hydride (1.29 g) dispersed in mineral oil (50% NaH) was added; and this mixture was warmed to 50° C., stirred for 1 hour, and cooled to room temperature. Methyl iodide (1.67 ml) was then added to the mixture, and the resulting mixture was stirred overnight at room temperature. A second portion (1.67 ml) of methyl iodide was added, and stirring was continued overnight. The mixture was filtered to separate a precipitate, and the filtrate was concentrated (under reduced pressure) to dryness. The filtrate residue was triturated with acetone to dissolve sodium iodide, and the insoluble white powder was dried in vacuo: yield, 4.66 g (82%); positive fast-atom-bombardment MS, m/e 225 (M+1), 247 (M+Na), 339 (247+glycerol), 431 (339+glycerol); negative fast-atom-bombardment MS, m/e 425, (2M - Na), 201 (M - Na), 293 (201+glycerol); $^1$H NMR (60 MHz, Me$_2$SO-D$_6$, Me$_4$Si as internal reference), δ1.50 (s, (CH$_3$)$_2$C), 3.08 (s, CH$_3$SO$_2$); IR (strong bands) 1310, 1295, 1235 sh, 1215, 1120, 1045, 730, 545 cm$^{-1}$. A portion of this material was recrystallized from ethanol, and the resulting white crystalline product was dried at 78° C. for 6 hours and at 100° C. for 4 hours: recovery, about 68%; mp 273°-279° C. Anal. Calcd. for C$_4$H$_9$O$_5$S$_2$Na. 0.25 H$_2$O: C, 21.00; H, 4.19. Found: C, 20.94; H, 4.48.

EXAMPLE 10

2-Chloroethyl (Methylsulfonyl)methanesulfonate; One step Synthesis.

A solution of 133 g (1.32 mol.) of triethylamine in 400 ml of anhydrous acetonitrile was cooled to −30° to −40° C., and a solution of 100 g (0.88 mol.) of methanesulfonyl chloride in anhydrous acetonitrile (67 ml) was added dropwise at a rate that prevented the temperature from rising above −30° C. The mixture was stirred at −30° to −40° C. for 1 hour, and a solution of 35.4 g of 2-chloroethanol in anhydrous acetonitrile (30 ml) was added. The resulting mixture was stirred for 2 hours at −30° to −40° C. and then was filtered to separate triethylamine hydrochloride. The latter material was washed with ethyl acetate, the washings were combined with the filtrate, and the organic solution was concentrated in vacuo to an oil. A solution of the residual oil in ethyl acetate (1200 ml) was washed quickly with two portions (2×200 ml) of dilute sodium chloride solution and then with two portions (2×200 ml) of saturated sodium chloride solution, dried with magnesium sulfate, filtered, and concentrated in vacuo. The residual solid (70 g) was dissolved in methylene chloride (450 ml), the solution was filtered and diluted slowly with cyclohexane (450 ml). The mixture, protected from atmospheric moisture, was allowed to stand at room temperature for about an hour and was then stored at low temperatures (about 5° C.) overnight. The precipitate was collected by filtration, washed with cyclohexane, and dried in vacuo over phosphorus pentoxide: yield, 58.7 g (56%); m.p. 60°-62° C.; IR (cm$^{-1}$, medium and strong bands) 3040, 3025, 2990 s, 2930, 2935 sh, 1465, 1430, 1415, 1390, 1370 s, 1320 s, 1240, 1200, 1185 s, 1175 s, 1165 s, 1125, 1070, 990 s, 955 s, 915 s, 870 s, 790 s, 765, 755, 665, 605 sh, 600, 525 s, 505, 465 s, 420; $^1$H NMR (300.6 MHz, CDCl$_3$, Me$_4$Si as internal reference), δ3.26 (s, CH$_3$), 3.80 (t, CH$_2$Cl), 4.65 (t, OCH$_2$), 4.67 (s, SCH$_2$S). Anal. Calcd. for C$_4$H$_9$ClO$_5$S$_2$ C, 20.30; H, 3.83. Found: C, 20.26; H, 4.00.

EXAMPLE 11

Tests of (Methylsulfonyl)methanesulfonates vs. P388 Leukemia In Vivo

The compounds of Examples 2–5 were administered intraperitoneally on days 1–5 after intraperitoneal inoculation of mice with 10$^6$ P388 leukemia cells. The results are set forth in Table I. For the compounds of Examples 2, 3 and 4, only those test results are set forth which resulted in at least one 30-day survivor. There were no survivors for the prior art compound of Example 5 after 30 days. Higher doses were not tested for the compound of Example 5 since this compound was toxic to the animals at 25 mg/kg/day.

TABLE I (Methylsulfonyl)methanesulfonates vs. P388 Leukemia In Vivo.[1,2]

| Compound Of Example | Experiment No. | Dose Mg/Kg/Day Q.D. 1-5[3] | Median Survival Time[4] of Control Mice, Days | Median Survival Time[4] of Non-Surviving (<60 days) Treated Mice, Days | Ratio of Median Survival Times[4] for Non-Survivors[5] T/C, % | Treated Mice 30-Day Survivors No./Total | 60-Day Survivors No./Total |
|---|---|---|---|---|---|---|---|
| 2. 2-Chloroethyl (methylsulfonyl) methanesulfonate | 1 | 50 | 11.2 | 31.5 | 281 | 4/6 | 2/6 |
| | 2 | 50 | 11.2 | 27.0 | 241 | 2/5 | 0/5 |
| | 4 | 50 | 10.5 | | | 6/6 | 6/6 |
| | | 33 | 10.5 | 21.5 | 205 | 1/6 | 0/6 |
| | 5 | 50 | 12.0 | 27.0 | 225 | 3/6 | 1/6 |
| | 6 | 50 | 13.0 | 43.5 | 335 | 5/6 | 2/6 |
| | 7 | 50 | 10.7 | | [6] | 4/6 | [7] |
| | 8 | 50 | 11.0 | 30.0 | 273 | 4/6 | 2/6 |
| 3. 2-Fluoroethyl (methylsulfonyl) methanesulfonate | 1 | 25 | 11.2 | 31.0[8] | 277[8] | 2/6 | 0/6 |
| | 2 | 50 | 10.5 | [9] | | 3/6 | 2/6 |
| | | 25 | 10.5 | 30.0 | 286 | 3/6 | 1/6 |
| 4. 2-Bromoethyl (methylsulfonyl) | 1 | 100 | 10.5 | 23.5 | 224 | 1/6 | 0/6 |
| | 2 | 100 | 13.0 | 7.0 | 54t | 1/6 | 0/6 |

TABLE I-continued (Methylsulfonyl)methanesulfonates vs. P388 Leukemia In Vivo.[1,2]

| Compound Of Example | Experiment No. | Dose Mg/Kg/Day Q.D. 1–5[3] | Median Survival Time[4] of Control Mice, Days | Median Survival Time[4] of Non-Surviving (<60 days) Treated Mice, Days | Ratio of Median Survival Times[4] for Non-Survivors[5] T/C, % | Treated Mice 30-Day Survivors No./Total | Treated Mice 60-Day Survivors No./Total |
|---|---|---|---|---|---|---|---|
| methanesulfonate |  |  |  |  |  |  |  |
| 5. Methyl | 1 | 25 | 10.7 |  | t | 0/6 | 0/6 |
| (methylsulfonyl) |  | 12 | 10.7 | 14.0 | 130 | 0/6 | 0/6 |
| methanesulfonate |  | 6 | 10.7 | 14.5 | 135 | 0/6 | 0/6 |
|  | 2 | 25 | 10.7 |  | t | 0/6 | 0/6 |
|  |  | 12 | 10.7 | 13.7 | 128 | 0/6 | 0/6 |
|  |  | 6 | 10.7 | 13.4 | 125 | 0/6 | 0/6 |

[1]Tests of these compounds against P388 Leukemia were performed in accordance with the protocols outlined by Geran et al in Cancer Chemotherapy Reports, Part 3, Volume 3, No. 2, pages 1–103 (1972), except for the calculation of median survival times of the groups of control animals and of those treated groups in which there were no 30-day survivors; see footnote 4.
[2]C = control groups of animals; T = treated groups. Mice in the treated and the control groups were inoculated intraperitoneally with $10^6$ P388 leukemia cells on Day 0. Members of the treated groups were treated on Days 1–5, inclusive, with the test compound at the specified doses.
[3]All compounds were administered within about five minutes of the preparation of solutions or suspensions.
[4]Median survival times of the untreated control groups and of the treated mice in those tests in which there were no 30-day survivors were calculated by considering the mortality data as grouped data. This method has been employed by the National Cancer Institute since about 1973. Median survival times for tests in which there were 30-day or 60-day survivors were calculated, as described by Geran et al, supra (Protocol 11), by considering the survival-time data as upgrouped data.
[5]t = toxic.
[6]One death on Day 6, one on Day 27, four 30-day survivors.
[7]Experiment terminated after 30 days.
[8]Based on the 4 of 6 that survived beyond Day 5.
[9]Day 32 was the day of death of the one animal that survived more than 6, but less than 60, days.

EXAMPLE 12

Inhibition of Other Cancers by 2-Chloroethyl (Methylsulfonyl)methanesulfonate

The compound of Example 2 also showed unusually high activity in inhibiting the development of other leukemias and tumors in mice. The exceptional activity by this compound against Melanotic Melanoma B16, Lymphoid Leukemia L1210, and Lewis Lung Carcinoma in mice is demonstrated by the results tabulated in Table II. These results show that the compound of Example 2 caused large increases in survival time of animals bearing these neoplasms. Furthermore, in several of the tests at 50 mg/kg/day or at 100 mg/kg/day 50–100% of the treated animals survived until the experiments were terminated after 60 days.

TABLE II

2-Chloroethyl (Methylsulfonyl)methanesulfonate (Example 2) vs. Other Cancers[1,2]

| Neoplasm | Dose Mg./Kg./Day Q.D. 1–9 | Sex of Treated Mice | Mortality By Day 5 Deaths/Total | Median Survival Time of Control Mice (C), Days | Median Survival Time of Treated Mice (T), Days[3] | Ratio of Survival Times T/C, % | 60-Day Survivors[4] No./Total |
|---|---|---|---|---|---|---|---|
| Melanotic | 100 | M | 2/10 | 18.1 | >60 | >331 | 7/10 |
| Melanoma, B16 | 50 | M | 0/10 | 18.1 | 49 | 270 | 1/10 |
|  | 25 | M | 0/10 | 18.1 | 32.3 | 178 | 0/10 |
|  | 100 | F | 2/10 | 17.4 | 8.3t |  |  |
|  | 50 | F | 0/10 | 17.4 | 39.8 | 229 | 0/10 |
|  | 25 | F | 0/10 | 17.4 | 29.5 | 169 | 0/10 |
| Lymphoid | 100 | F | 0/6 | 8.5 | 49.5 | 582 | 3/6 |
| Leukemia L1210 | 50 | F | 0/6 | 8.5 | 44.5 | 524 | 3/6 |
|  | 25 | F | 0/6 | 8.5 | 16.8 | 198 |  |
|  | 100 | M | 2/6 | 8.3 | 6.7t |  |  |
|  | 50 | M | 0/6 | 8.3 | >60 | >722 | 6/6 |
|  | 25 | M | 0/6 | 8.3 | 19.0 | 229 | 0/6 |
| Lewis Lung | 100 | F | 0/9 | 16.3 | 30.5 | 187 | 2/9 |
| Carcinoma | 50 | F | 0/10 | 16.3 | 25.3 | 155 | 0/10 |
|  | 25 | F | 0/10 | 16.3 | 19.3 | 118 | 0/10 |
|  | 100 | M | 0/10 | 21.1 | 12.0t |  |  |
|  | 50 | M | 0/10 | 21.1 | >60 | >284 | 6/10 |
|  | 25 | M | 0/10 | 21.1 | 27.8 | 132 | 0/10 |

[1]Tests of the compound of Example 2 against the mouse neoplasms listed in this table were performed in accordance with the protocols outlined by Geran et al. in Cancer Chemotherapy Reports, Part 3, Volume 3, No. 2, pages 1–103 (1972).
[2]C = Control group; a group of untreated mice bearing the specified neoplasm. T = Treated group; a group of mice bearing the same tumor, but treated with 2-chloroethyl (methylsulfonyl)methanesulfonate. Both the control and the treated groups were implanted with the neoplasm on Day 0.
[3]t = toxic
[4]The number of treated mice that were alive on Day 60, at which time the experiment was terminated.

We claim:

1. Compounds having the formula:

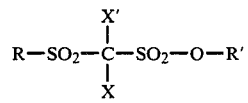

wherein R is a lower alkyl group; X and X' individually are hydrogen or lower alkyl, and R' is a halogenated lower alkyl group.

2. A compound as defined in claim 1 wherein R is methyl.

3. A compound as defined in claim 2 wherein X and X' are hydrogen.

4. A compound as defined in claim 3 wherein R' is a 2-haloethyl group.

5. A compound as defined in claim 1 wherein R and X are methyl groups and X' is hydrogen.

6. A compound as defined in claim 5 wherein R' is a 2-haloethyl group.

7. 2-Chloroethyl (methylsulfonyl)methanesulfonate.
8. 2-Fluoroethyl (methylsulfonyl)methanesulfonate.
9. 2-Bromoethyl (methylsulfonyl)methanesulfonate.
10. 2-Chloroethyl 1-(methylsulfonyl)ethanesulfonate.
11. 2-Chloroethyl 1-methyl-1-(methylsulfonyl)ethanesulfonate.

* * * * *